United States Patent
Liu et al.

(10) Patent No.: US 11,959,900 B2
(45) Date of Patent: Apr. 16, 2024

(54) HEALTH EARLY WARNING SYSTEM FOR PASSENGERS ON A TRAIN IN AN OUTDOOR AIR POLLUTED ENVIRONMENT AND METHOD THEREOF

(71) Applicant: Central South University, Hunan (CN)

(72) Inventors: Hui Liu, Hunan (CN); Haiping Wu, Hunan (CN); Yanfei Li, Hunan (CN); Chao Chen, Hunan (CN)

(73) Assignee: Central South University, Hunan (CN)

( * ) Notice: Subject to any disclaimer, the term of this patent is extended or adjusted under 35 U.S.C. 154(b) by 518 days.

(21) Appl. No.: 17/291,619

(22) PCT Filed: Jul. 13, 2020

(86) PCT No.: PCT/CN2020/101735
§ 371 (c)(1),
(2) Date: May 6, 2021

(87) PCT Pub. No.: WO2021/012982
PCT Pub. Date: Jan. 28, 2021

(65) Prior Publication Data
US 2022/0011284 A1    Jan. 13, 2022

(30) Foreign Application Priority Data
Jul. 25, 2019   (CN) .......................... 201910676714.7

(51) Int. Cl.
*G01N 33/00* (2006.01)
*B61L 25/02* (2006.01)
*B61L 27/70* (2022.01)

(52) U.S. Cl.
CPC ........ *G01N 33/0063* (2013.01); *B61L 25/021* (2013.01); *B61L 25/025* (2013.01); *B61L 27/70* (2022.01); *G01N 33/0075* (2013.01)

(58) Field of Classification Search
CPC ........... G01N 33/0063; G01N 33/0075; B61L 25/021; B61L 25/025; B61L 27/70
See application file for complete search history.

(56) References Cited

FOREIGN PATENT DOCUMENTS

| CN | 104236031 | 12/2014 |
|----|-----------|---------|
| CN | 105954166 | 9/2016  |

(Continued)

OTHER PUBLICATIONS

English translation of CN105966195 (Year: 2016).*

(Continued)

*Primary Examiner* — Nabil H Syed
*Assistant Examiner* — Cal J Eustaquio
(74) *Attorney, Agent, or Firm* — JCIP GLOBAL INC.

(57) ABSTRACT

A health early warning system for passengers on a train in an outdoor air polluted environment and a method thereof are provided. The system comprises an air quality monitoring station data acquisition module, a train data acquisition module, a train air pollution prediction module, and a train air environment early warning module; the air quality monitoring station data acquisition module acquires data of air quality monitoring stations and uploads the data to the train air pollution prediction module; the train data acquisition module acquires data of the train and uploads the data to the train air pollution prediction module; the train air pollution prediction module performs short-term prediction on air pollution of the train and uploads a result of the short-term prediction to the train air environment early warning module; and the train air environment early warning module performs early warning on the health of the passengers on the train.

8 Claims, 2 Drawing Sheets

(56) References Cited

FOREIGN PATENT DOCUMENTS

| | | |
|---|---|---|
| CN | 105966195 | 9/2016 |
| CN | 106651100 | 5/2017 |
| CN | 106975279 | 7/2017 |
| CN | 107167178 | 9/2017 |
| CN | 105172818 | 2/2018 |
| CN | 110361505 | 10/2019 |
| JP | 2000193651 | 7/2000 |

OTHER PUBLICATIONS

English translation of CN104236031 (Year: 2014).*
"International Search Report (Form PCT/ISA/210) of PCT/CN2020/101735," dated Oct. 20, 2020, with English translation thereof, pp. 1-6.

* cited by examiner

HEALTH EARLY WARNING SYSTEM FOR PASSENGERS ON A TRAIN IN AN OUTDOOR AIR POLLUTED ENVIRONMENT AND METHOD THEREOF

CROSS-REFERENCE TO RELATED APPLICATION

This application is a 371 of international application of PCT application serial no. PCT/CN2020/101735, filed on Jul. 13, 2020, which claims the priority benefit of China application no. 201910676714.7, filed on Jul. 25, 2019. The entirety of each of the above mentioned patent applications is hereby incorporated by reference herein and made a part of this specification.

BACKGROUND

Technical Field

The present invention specifically relates to a health early warning system for passengers on a train in an outdoor air polluted environment and a method thereof.

Description of Related Art

With the development of technology and the improvement of people's standards of living, transportation has become one of the most important components of modern society. And with the development of technology, the railway industry in China has also been greatly developed.

Train ventilation is one of the important means to guarantee normal operation of a train and to ensure comfort of passengers thereon. With the increasing emphasis on reducing environmental pollution and the continued concern for health, environmental pollution inside a train has also been brought to public attention.

At present, since nearly all train carriages in China are enclosed, pollutants such as PM2.5 and the like therein are not easy to be purified. According to current technologies, control of train air pollution is mainly achieved by installing novel vehicle-mounted air purifying apparatuses. For example, the patent with the publication number of 105172818B provides a special air purifier for trains, which comprises an upper box body, and a lower box body matching with the upper box body. The patent with the publication number of 106975279A provides an air purifying apparatus, system and method for high-speed trains, and the air purifying apparatus comprises an air inlet passage and a filter screen assembly. These methods are for purifying indoor air pollutants of a train and no consideration is taken from the perspective of real-time monitoring of outdoor air pollutants of the train. Moreover, these methods can be only used for purifying air in a carriage of a train, but cannot perform early warning on an indoor air environment of the train.

SUMMARY

One purpose of the present invention is to provide a health early warning system for passengers on a train in an outdoor air polluted environment, which can be used for performing early warning on an indoor air environment of the train and on health of the passengers on the train with high reliability and good accuracy.

A second purpose of the present invention is to provide a method used by the health early warning system for passengers on a train in an outdoor air polluted environment.

The health early warning system for passengers on a train in an outdoor air polluted environment provided by the present invention comprises an air quality monitoring station data acquisition module, a train data acquisition module, a train air pollution prediction module and a train air environment early warning module, wherein an output end of the air quality monitoring station data acquisition module and an output end of the train data acquisition module are both connected with an input end of the train air pollution prediction module; an output end of the train air pollution prediction module is connected with the train air environment early warning module; the air quality monitoring station data acquisition module is configured to acquire data information of air quality monitoring stations and upload the data information to the train air pollution prediction module; the train data acquisition module is configured to acquire data information of the train and upload the data information to the train air pollution prediction module; the train air pollution prediction module is configured to perform short-term prediction on air pollution of the train according to the uploaded data information and upload a predicted result to the train air environment early warning module; and the train air environment early warning module is configured to perform air environment early warning according to the predicted result, thereby performing early warning on an air environment of the train and on health of the passengers on the train.

The present invention also provides a method used by the health early warning system for passengers on a train in an outdoor air polluted environment, which comprises the following steps:

S1. acquire data information of each air quality monitoring station and corresponding air quality monitoring data thereof;
S2. acquire pollutant data information of a position where the train is located and position information of the train;
S3. perform train-air quality monitoring station coupling analysis according to data acquired in the steps S1 and S2, thereby screening out a plurality of associated air quality monitoring stations;
S4. establish a spatial mixture model for multi-pollutant concentration indexes according to the plurality of associated air quality monitoring stations screened out in the step S3;
S5. perform short-term prediction on air pollutant concentrations of the position where the train is located by using the spatial mixture model for multi-pollutant concentration indexes established in the step S4; and
S6. perform early warning on an air environment of the train according to a result of the short-term prediction in the step S5.

The step of acquiring data information of each air quality monitoring station and corresponding air quality monitoring data thereof in the step S1 is, specifically, to acquire code information, longitude and latitude information, as well as corresponding information of concentrations of PM2.5, PM10, CO, $NO_2$, $SO_2$ and $O_3$ and AQIs of each air quality monitoring station.

The step of acquiring pollutant data information of a position where the train is located and position information of the train in the step S2 is, specifically, to acquire longitude and latitude information, information of concentrations of PM2.5, PM10, CO, $NO_2$, $SO_2$ and $O_3$ of the position where the train is located, and information of average speed per minute of the train in past several minutes, and information of a directed path of a remaining running route of the train.

The step of performing train-air quality monitoring station coupling analysis in the step S3, thereby screening out a plurality of associated air quality monitoring stations, is, specifically, to perform the coupling analysis and screen out the associated air quality monitoring stations in the following steps:

A. calculate a predicted position of the train after future T minutes, wherein T is a positive integer;
B. calculate a distance between the train and each air quality monitoring station after the future T minutes;
C. calculate mutual information between pollutant data information on the train side and air quality monitoring data of each air quality monitoring station at a plurality of continuous moments, thereby obtaining a deterministic association index set between the train side and each air quality monitoring station; and
D. analyze and select a plurality of associated air quality monitoring stations with the greatest environmental impact on the train side after the T minutes according to the distance between the train and each air quality monitoring station.

The step of calculating a predicted position of the train after future T minutes in the step A is, specifically, to calculate the predicted position of the train after the future T minutes by using the following equation:

$$LOC_T^C = [LOT^C + T \times v \times \vec{r}_{LOT}, LAT^C + T \times v \times \vec{r}_{LAT}]$$

wherein, $LOC_T^C$ is longitude and latitude information of the predicted position of the train after the future T minutes; $LOT^C$ is current longitude information of the train, $LAT^C$ is current latitude information of the train, v is the information of average speed per minute of the train in past several minutes, $\vec{r}_{LOT}$ is a longitude unit vector of the directed path of the remaining running route of the train, and $\vec{r}_{LAT}$ is a latitude unit vector of the directed path of the remaining running route of the train.

The step of calculating mutual information between pollutant data information on the train side and air quality monitoring data of each air quality monitoring station at a plurality of continuous moments in the step C is, specifically, to calculate the mutual information by using the following equation:

$$MI(A_{200}^C; A_{200}^{S,i}) = \sum_{a \in A_{200}^C} \sum_{b \in A_{200}^{S,i}} P(a,b) \log \frac{P(a,b)}{P(a)P(b)} = H(A_{200}^C) - H(A_{200}^C | A_{200}^{S,i})$$

wherein, $A_{200}^C$ is an AQI sequence on the train side in 200 continuous moments, $A_{200}^{S,i}$ is an AQI value of the i-th air quality monitoring station; P(a,b) is a joint probability distribution function of random variables $A_{200}^C$ and $A_{200}^{S,i}$, P(a) is a marginal probability distribution function of $A_{200}^C$, P(b) is a marginal probability distribution function of $A_{200}^{S,i}$, $H(A_2O_0)$ is a marginal entropy, and $H(A_{200}^C | A_{200}^{S,i})$ is a conditional entropy.

The step of analyzing and selecting a plurality of associated air quality monitoring stations with the greatest environmental impact on the train side after the T minutes in the step D is, specifically, to perform analysis and selection in the following steps:

a. calculate a degradation degree $E_T^i$ imposed by each air quality monitoring station on air quality on the train side after the T minutes by using the following equation:

$$E_T^i = \frac{p}{Nd_T^i} + (1-p) \times NMI(A_{200}^C; A_{200}^{S,i})$$

wherein, $Nd_T^i$ is a relative distance between a normalized air quality monitoring station i and the train after the T minutes; p is a diffusion factor; and $NMI(A_{200}^C; A_{200}^{S,i})$ is the mutual information between the normalized air quality monitoring station i and the train.

b. optimize a value of the diffusion factor by using a multi-objective and multi-verse optimization algorithm; and
c. select, according to the degradation degree calculated in the step a, a plurality of air quality monitoring stations imposing the greatest degradation degree as final air quality monitoring stations with the greatest environmental impact on the train side.

The step of optimizing a value of the diffusion factor by using a multi-objective and multi-verse optimization algorithm in the step b is, specifically, to perform optimization in the following steps:

(1) establish a single-variable optimization model, wherein an optimization variable is the diffusion factor p;
(2) initialize the algorithm, and set an algorithm parameter;
(3) arrange and archive all universe groups by expansion rate;
(4) screen out an optimal universe from a Pareto solution set as a universal leader;
(5) open a black-white hole tunnel and a wormhole tunnel, wherein objects in the universe can pass through the tunnels self-adaptively until a lower expansion rate is acquired; and
6) determine a search frequency:
if the search frequency reaches a set threshold, output an optimal solution for determining the value of the diffusion factor;
otherwise, add 1 to the search frequency, and repeat the steps (3) to (6) until the search frequency reaches the set threshold.

The step of establishing a spatial mixture model for multi-pollutant concentration indexes in the step S4 is, specifically, to establish the model in the following steps:

1) acquire air quality data information of the associated air quality monitoring stations and pollutant data information of the train;
2) divide data acquired in the step 1) into a training set and a verification set;
3) train a predictor model by taking the air quality data information of the associated air quality monitoring stations as an input of the predictor model, and by taking the pollutant data information of the train after a $\Delta t$ moment as an output of the predictor model, thereby obtaining a pollutant concentration prediction model for the associated air quality monitoring stations in a step of $\Delta t$;
4) perform, according to the pollutant concentration prediction model for the associated air quality monitoring stations obtained in the step 3), a plurality of steps of prediction on air quality of the positions where the associated air quality monitoring stations are located, thereby obtaining an air quality prediction set of the associated air quality monitoring stations; and 5) train and establish a deep belief network model by taking a multiplication combination term of the air quality data information of the associated air quality monitoring stations and a degradation degree imposed by the associated air quality monitoring stations on the air quality on the train side after the T minutes as an input of the deep belief network model and by taking the pollutant data information on the train side as an output of the deep belief network model, thereby obtaining the spatial mixture model for multi-pollutant concentration indexes.

The step of obtaining a pollutant concentration prediction model for the associated air quality monitoring stations in a step of Δt in the step 3) is, specifically, to use a GMDH predictor as a predictor model, which uses a Kolmogorov-Gabor polynomial as a support function; a topological structure of the GMDH predictor comprises 3 layers, and the model selects a plurality of neurons as an input of the next layer after a first layer is formed; the number of neurons in each layer is limited to 100; and the following equation is used as an evaluation function:

$$\text{evaluation} = \sum_{i=1}^{3} n_i + MSE$$

wherein, $n_i$ is the number of neurons in the i-th layer in the GMDH predictor, and MSE is a mean square error predicted by the prediction model on the verification set.

The step of performing early warning on an air environment of the train in the step S6 is, specifically, to perform the early warning in the following rules:

if predicted AQI values of an area passed by the train are smaller than or equal to 100 within a plurality of future moments, an air pollution level is predicted to be 0, and the early warning will not be performed;

if the predicted AQI values of the area passed by the train are greater than 100 but smaller than or equal to 200 within the plurality of future moments, the air pollution level is predicted to be 1, and a level-1 early warning will be performed; and if the predicted AQI values of the area passed by the train are greater than 200 within the plurality of future moments, the air pollution level is predicted to be 2, and a level-2 early warning will be performed; and According to the health early warning system for passengers on a train in an outdoor air polluted environment and method thereof provided by the present invention, based on a fusion result of train-station distance and association, a degradation degree imposed by each air quality monitoring station on air quality on the train side after a certain period of time is calculated by utilizing acquired real-time monitoring data of the air quality monitoring stations and installing a vehicle-mounted air quality data acquisition module in each carriage of the train; a spatial mixture model for multi-pollutant concentration indexes is established by selecting the monitoring stations with the greatest impact on outdoor air quality of the train to perform short-term prediction on outdoor air pollutant concentrations of the train. Therefore, the present invention can be used for performing early warnings on the health of the passengers on the train with high reliability and good accuracy.

DESCRIPTION OF THE EMBODIMENTS

Figure 1:
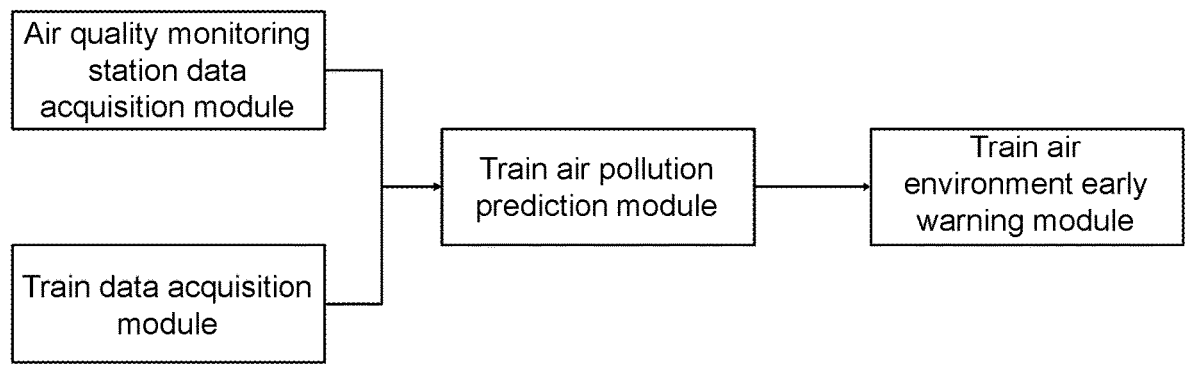
FIG. 1 is a functional module diagram of the system according to the present invention.

As shown in the functional module diagram of the system according to the present invention in FIG. 1: the health early warning system for passengers on a train in an outdoor air polluted environment provided by the present invention comprises an air quality monitoring station data acquisition module, a train data acquisition module, a train air pollution prediction module and a train air environment early warning module, wherein an output end of the air quality monitoring station data acquisition module and an output end of the train data acquisition module are both connected with an input end of the train air pollution prediction module; an output end of the train air pollution prediction module is connected with the train air environment early warning module; the air quality monitoring station data acquisition module is configured to acquire data information of air quality monitoring stations and upload the data information to the train air pollution prediction module; the train data acquisition module is configured to acquire data information of the train and upload the data information to the train air pollution prediction module; the train air pollution prediction module is configured to perform short-term prediction on air pollution of the train according to the uploaded data information and upload a predicted result to the train air environment early warning module; and the train air environment early warning module is configured to perform air environment early warning according to the predicted result, thereby performing early warning on an air environment of the train and on health of the passengers on the train.

Figure 2:
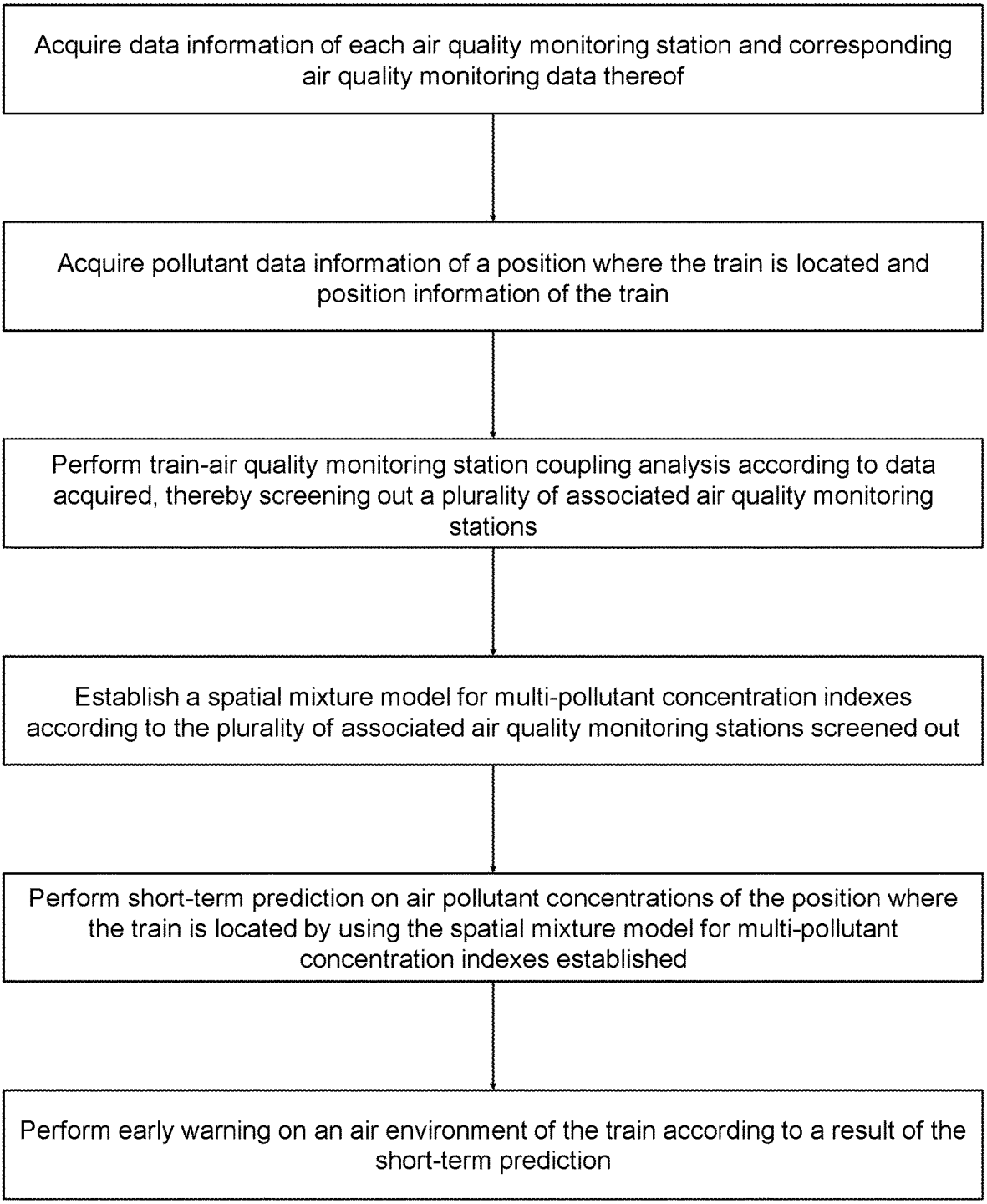
FIG. 2 is a flowchart of the method according to the present invention.

As shown in the flowchart of the method according to the present invention in FIG. 2: the present invention also provides a method used by the health early warning system for passengers on a train in an outdoor air polluted environment, which comprises the following steps:

S1. acquire data information of each air quality monitoring station and corresponding air quality monitoring data thereof; specifically, it is to acquire code information, longitude and latitude information, as well as corresponding information of concentrations of PM2.5, PM10, CO, $NO_2$, $SO_2$ and $O_3$ and AQIs of each air quality monitoring station;

in specific implementations, concentrations of PM2.5, PM10, CO, $NO_2$, $SO_2$ and $O_3$ and AQI of N air quality monitoring stations at T continuous moments are acquired and can be expressed as $$D_T^N = [C_{PM2.5}, C_{PM10}, C_{CO}, C_{NO2}, C_{SO2}, C_{O3}, AQI]_T^N$$

and meanwhile, code and longitude and latitude information of the air quality monitoring stations need to be added during storage, so that the data information can be stored as $$X_T^N = [C_{PM2.5}, C_{PM10}, C_{CO}, C_{NO2}, C_{SO2}, C_{O3}, AQI, \text{Code}, LOT^S, LAT^S]_T^N$$

wherein, Code is a code of each air quality monitoring station, and $LOT^S$ and $LAT^S$ are longitude and latitude information of each air quality monitoring station; and each piece of monitoring data needs to correspond to the code, longitude and latitude of each monitoring station, a timestamp of each piece of monitoring data is recorded, and the interval between adjacent data is acquisition time interval data, which can be selected as 1 hour;

S2. acquire pollutant data information of a position where the train is located and position information of the train; specifically, it is to acquire longitude and latitude information, information of concentrations of PM2.5, PM10, CO, NO$_2$, SO$_2$ and O$_3$ of the position where the train is located, and information of average speed per minute of the train in past several minutes, and information of a directed path of a remaining running route of the train;

in specific implementations, related outdoor pollutant indexes of the train comprise concentrations of PM2.5, PM10, CO, NO$_2$, SO$_2$ and O$_3$ at the T continuous moments, which can be expressed as $d_T^N = [C_{PM2.5}, C_{PM10}, C_{CO}, C_{NO2}, C_{SO2}, C_{O3}]_T$; meanwhile, an AQI at each moment can be calculated by utilizing the concentrations of the above-mentioned 6 pollutants; a sampling interval is kept consistent with that of an existing air quality monitoring station, that is, pollutant concentration monitoring is carried out once at each hour; and meanwhile, longitude and latitude data $[LOT^C, LAT^C]$ of the train in the T continuous moments are recorded; in addition, the information of average speed per minute of the train in past 60 minutes and the information of a directed path (including longitude and latitude unit vectors $\vec{r}_{LOT}$ and $\vec{r}_{LAT}$ of the train in a forward direction at any time) of a remaining running route of the train need to be recorded;

S3. perform train-air quality monitoring station coupling analysis according to data acquired in the steps S1 and S2, thereby screening out a plurality of associated air quality monitoring stations; specifically, it is to perform the coupling analysis and screen out the associated air quality monitoring stations in the following steps:

A. calculate a predicted position of the train after future T minutes, wherein T is a positive integer; specifically, it is to calculate the predicted position of the train after the future T minutes by using the following equation:

$$LOC_T^C = [LOT^C + T \times v \times \vec{r}_{LOT}, LAT^C + T \times v \times \vec{r}_{LAT}]$$

wherein, $LOC_T^C$ is longitude and latitude information of the predicted position of the train after the future T minutes; $LOT^C$ is current longitude information of the train, $LAT^C$ is current latitude information of the train, v is the information of average speed per minute of the train in past several minutes, $\vec{r}_{LOT}$ is a longitude unit vector of the directed path of the remaining running route of the train, and $\vec{r}_{LAT}$ is a latitude unit vector of the directed path of the remaining running route of the train;

B. calculate a distance between the train and each air quality monitoring station after the future T minutes;

$$d_T^m = \sqrt{(LOC_T^C(1) - LOT^{S,m})^2 + (LOC_T^C(2) - LAT^{S,m})^2}$$

wherein, $d_T^m$ is a relative distance between the train and the air quality monitoring station m; and a train-station real-time distance index set distance$_T = [d_T^1, d_T^2, \ldots, d_T^N]$ is obtained after calculating the distances between the train and all of the N air quality monitoring stations;

C. calculate mutual information between pollutant data information on the train side and air quality monitoring data of each air quality monitoring station at a plurality of continuous moments, thereby obtaining a deterministic association index set between the train side and each air quality monitoring station; specifically, it is to calculate the mutual information by using the following equation:

$$MI(A_{200}^C; A_{200}^{S,i}) = \sum_{a \in A_{200}^C} \sum_{b \in A_{200}^{S,i}} P(a,b) \log \frac{P(a,b)}{P(a)P(b)} = H(A_{200}^C) - H(A_{200}^C | A_{200}^{S,i})$$

wherein, $A_{200}^C$ is an AQI sequence on the train side in 200 continuous moments, $A_{200}^{S,i}$ is an AQI value of the i-th air quality monitoring station; P(a,b) is a joint probability distribution function of random variables $A_{200}^C$ and $A_{200}^{S,i}$, P(a) is a marginal probability distribution function of $A_{200}^C$, P(b) is a marginal probability distribution function of $A_{200}^{S,i}$, $H(A_2O_0)$ is a marginal entropy, and $H(A_{200}^C | A_{200}^{S,i})$ is a conditional entropy;

meanwhile, after performing association analysis on all air quality monitoring stations, an index set of mutual information between air quality indexes of all air quality monitoring stations and the train, wherein the index set of mutual information can be expressed as $$MI^N = [MI(A_{200}^C; A_{200}^{S,1}), MI(A_{200}^C; A_{200}^{S,2}), \ldots, MI(A_{200}^C; A_{200}^{S,n})];$$

D. analyze and select a plurality of associated air quality monitoring stations with the greatest environmental impact on the train side after the T minutes according to the distance between the train and each air quality monitoring station; specifically, it is to perform analysis and selection in the following steps:

a. calculate a degradation degree $E_T^i$ imposed by each air quality monitoring station on air quality on the train side after the T minutes by using the following equation:

$$E_T^i = \frac{p}{Nd_T^i} + (1-p) \times NMI(A_{200}^C; A_{200}^{S,i})$$

wherein, $Nd_T^i$ is a relative distance between a normalized air quality monitoring station i and the train after the T minutes; p is a diffusion factor; and $NMI(A_{200}^C; A_{200}^{S,i})$ is mutual information between the normalized air quality monitoring station i and the train.

b. optimize a value of the diffusion factor by using a multi-objective and multi-verse optimization algorithm; specifically, it is to perform optimization in the following steps:

(1) establish a single-variable optimization model, wherein an optimization variable is the diffusion factor p;

in specific implementations, for each individual in a multi-verse universe group, fitness needs to be calculated so as to measure quality of an optimization effect; in order to ensure effectiveness of a degradation degree index, maximizing combination of degradation degrees of all monitoring stations and minimizing difference between the degradation degrees are used as a search direction for evaluating each universe, and a corresponding fitness function is as follows:

$$\begin{cases} \text{fitness1} = \max\sum_{i=1}^{N} E_T^i = \max\sum_{i=1}^{N}\left(\frac{p}{Nd_T^i} + (1-p)\times NMI\left(A_{200}^C; A_{200}^{S,i}\right)\right) \\ \text{fitness2} = \min\sum_{i=1}^{N}\sum_{j=1}^{N}\left|E_T^i - E_T^j\right| = \min\sum_{i=1}^{N}\sum_{j=1}^{N}\left|\frac{p}{Nd_T^i} + (1-p)\times NMI\left(A_{200}^C; A_{200}^{S,i}\right) - \frac{p}{Nd_T^i} - (1-p)\times NMI\left(A_{200}^C; A_{200}^{S,j}\right)\right| \end{cases}$$

(2) initialize the algorithm, and set an algorithm parameter;

in specific implementations, a value range of multi-verse positions is set as [0,1], the number of groups is set as 200, an iteration threshold is set as 100, and an archiving threshold of a Pareto solution is 100. 200 multi-verse universes are randomly initialized as initial diffusion factors to calculate an expansion rate of each universe (fitness);

(3) arrange and archive all universe groups by expansion rate;

determine solution set dominance, store a dominant solution and a universe with the lowest expansion rate, and record an archiving number as Ar; if Ar is greater than the archiving threshold of the Pareto solution, a solution with a higher expansion rate is abandoned;

(4) screen out an optimal universe from a Pareto solution set (by the roulette wheel selection method) as a universe leader;

(5) open a black-white hole tunnel and a wormhole tunnel, wherein objects in the universe can pass through the tunnels self-adaptively until a lower expansion rate is acquired; and 6) determine a search frequency:

if the search frequency reaches a set threshold, output an optimal solution for determining the value of the diffusion factor;

otherwise, add 1 to the search frequency, and repeat the steps (3) to (6) until the search frequency reaches the set threshold;

according to an obtained optimal diffusion factor, perform distance-association fusion on all monitoring stations, thereby obtaining a set of degradation degrees $[E_T^1, E_T^2, \ldots, E_T^N]$ imposed by all monitoring stations on the air quality on the train side; and c. select, according to the degradation degree calculated in the step a, a plurality of air quality monitoring stations imposing the greatest degradation degree as final air quality monitoring stations with the greatest environmental impact on the train side;

in specific implementations, 5 monitoring stations imposing the greatest degradation degree are recorded as ε1, ε2, ε3, ε4, ε5, and can be regarded as a spatially related data set of the outdoor air environment of the train since the stations are close to the position where the train is located after the T moments and have the greatest impact degree on the outdoor air quality of the train after the T moments;

S4. establish a spatial mixture model for multi-pollutant concentration indexes according to the plurality of associated air quality monitoring stations screened out in the step S3; specifically, it is to establish the model in the following steps:

1) acquire air quality data information of the associated air quality monitoring stations and pollutant data information of the train;

based on the 5 air quality monitoring stations ε1, ε2, ε3, ε4, ε5 imposing the greatest degradation degree on the air quality on the train side in A4, record codes of the monitoring stations as Code1,Code2,Code3,Code4,Code5 align the codes with real-time monitoring records in a big data storage platform, read an index set of concentrations of PM2.5, PM10, CO, $NO_2$, $SO_2$ and $O_3$ and AQIs of the 5 air quality monitoring stations in 200 continuous moments, and record it as $D_{200}^{\varepsilon1,\varepsilon2,\varepsilon3,\varepsilon4,\varepsilon5} = [C_{PM2.5}, C_{PM10}, C_{CO}, C_{NO2}, C_{SO2}, C_{O3}, AQI]_{200}^{\varepsilon1,\varepsilon2,\varepsilon3,\varepsilon4,\varepsilon5}$; and read an index set of $g_{200} = [C_{PM2.5}, C_{PM10}, C_{CO2}, C_{NO2}, C_{SO2}, C_{O3}, AQI]_{200}$ concentrations of PM2.5, PM10, CO, $NO_2$, $SO_2$ and $O_3$ and AQI on the train end;

2) divide data acquired in the step 1) into a training set and a verification set;

in specific implementations, model data is from a vehicle-mounted air quality data acquisition module and 5 spatially related monitoring stations, a data set of each monitoring point comprises 7 indexes of 200 historical continuous moments and can be recorded as R(C, ε1, ε2, ε3, ε4, ε5, 7, 200); and data of the first 160 moments is used as the training set, and data of the last 40 moments is used as the verification set;

3) train a predictor model by taking the air quality data information of the associated air quality monitoring stations as an input of the predictor model, and by taking the pollutant data information of the train after a Δt moment as an output of the predictor model, thereby obtaining a pollutant concentration prediction model for the associated air quality monitoring stations in a step of Δt; specifically, it is to use a GMDH predictor as a predictor model, which uses a Kolmogorov-Gabor polynomial as a support function; a topological structure of the GMDH predictor comprises 3 layers, and the model selects a plurality of neurons as an input of the next layer after a first layer is formed; the number of neurons in each layer is limited to 100; and the following equation is used as an evaluation function:

$$\text{evaluation} = \sum_{i=1}^{3} n_i + MSE$$

wherein, $n_i$ is the number of neurons in the i-th layer in the GMDH predictor, and MSE is a mean square error predicted by the prediction model on the verification set;

in specific implementations, 7*5-dimensional pollutant index vectors of the 5 spatially related monitoring stations in the first 160 moments in the data set are used as the input of the GMDH predictor, correspondingly, sequences of PM2.5, PM10, CO, $NO_2$, $SO_2$, $O_3$ and AQI of the first 160 moments after Δt in a sample are used as the output of the predictor model, thereby obtaining the pollutant concentration prediction model for the air quality monitoring stations in a step of Δt; by using the Kolmogorov-Gabor polynomial as the support function, the GMDH predictor increases complexity of the model and solves a relationship between the input and the output self-adaptively; by arranging the GMDH predictor with a three-layer topological structure, the model selects a plurality of neurons as the input of the next layer after the first layer is formed; the process is cyclically executed to obtain a model with optimal complexity; and for limiting training time of the model, the number of neurons in each layer is limited to 100. For achieving balance between model complexity and precision, weighted combination of the layer-averaged number of neurons of GMDH and a mean square error (MSE) predicted on the verification set is taken as the evaluation function of the model as follows:

$$\text{evaluation} = \sum_{i=1}^{3} n_i + MSE = \sum_{i=1}^{3} n_i + \frac{1}{40}\sum_{t=1}^{40}(f(t) - Y(t))^2$$

wherein, $n_i$ is the number of neurons in the i-th layer in the GMDH predictor, and MSE is the mean square error predicted by the prediction model on the verification set; and f(t) is a predicted result of the predictor on the verification set, and Y(t) is actual verification set data;

4) perform, according to the pollutant concentration prediction model for the associated air quality monitoring stations obtained in the step 3), a plurality of steps of prediction on air quality of the positions where the associated air quality monitoring stations are located, thereby obtaining an air quality prediction set of the associated air quality monitoring stations; and in specific implementations, the model with the lowest evaluation value is selected as a final air pollutant prediction model for the monitoring stations, which has better prediction performance and lower model complexity; based on the air pollutant prediction model for the monitoring stations, multi-step prediction in a time step of 15 minutes, 30 minutes, 45 minutes and 60 minutes is performed on air pollutant indexes of the positions where the ε1, ε2, ε3, ε4, ε5 5 monitoring stations are located, thereby obtaining a pollutant concentration prediction set of the monitoring stations:

$$\begin{cases} F_{15min}^{\varepsilon1,\varepsilon2,\varepsilon3,\varepsilon4,\varepsilon5} = [\hat{C}_{PM25}, \hat{C}_{PM10}, \hat{C}_{CO}, \hat{C}_{NO2}, \hat{C}_{SO2}, \hat{C}_{O3}, \hat{AQI}]_{15min}^{\varepsilon1,\varepsilon2,\varepsilon3,\varepsilon4,\varepsilon5} \\ F_{30min}^{\varepsilon1,\varepsilon2,\varepsilon3,\varepsilon4,\varepsilon5} = [\hat{C}_{PM25}, \hat{C}_{PM10}, \hat{C}_{CO}, \hat{C}_{NO2}, \hat{C}_{SO2}, \hat{C}_{O3}, \hat{AQI}]_{30min}^{\varepsilon1,\varepsilon2,\varepsilon3,\varepsilon4,\varepsilon5} \\ F_{45min}^{\varepsilon1,\varepsilon2,\varepsilon3,\varepsilon4,\varepsilon5} = [\hat{C}_{PM25}, \hat{C}_{PM10}, \hat{C}_{CO}, \hat{C}_{NO2}, \hat{C}_{SO2}, \hat{C}_{O3}, \hat{AQI}]_{45min}^{\varepsilon1,\varepsilon2,\varepsilon3,\varepsilon4,\varepsilon5} \\ F_{60min}^{\varepsilon1,\varepsilon2,\varepsilon3,\varepsilon4,\varepsilon5} = [\hat{C}_{PM25}, \hat{C}_{PM10}, \hat{C}_{CO}, \hat{C}_{NO2}, \hat{C}_{SO2}, \hat{C}_{O3}, \hat{AQI}]_{60min}^{\varepsilon1,\varepsilon2,\varepsilon3,\varepsilon4,\varepsilon5} \end{cases}$$

5) train and establish a deep belief network model by taking a multiplication combination term of the air quality data information of the associated air quality monitoring stations and a degradation degree imposed by the associated air quality monitoring stations on the air quality on the train side after the T minutes as an input of the deep belief network model and by taking the pollutant data information on the train side as an output of the deep belief network model, thereby obtaining the spatial mixture model for multi-pollutant concentration indexes;

in specific implementations, for a pollutant monitoring result of each monitoring station, the deep belief network is constructed so as to obtain a high-precision spatial mixture model; the number of nodes in hidden layers are set as 50, 100 and 50 respectively by using a three-layer stacked deep belief network; and the multiplication combination term of the pollutant indexes of spatially related monitoring stations and the degradation degree imposed by the monitoring stations on the outdoor pollutants of the train is set as the input of the deep belief network model $$\underset{ER}{\Leftrightarrow}(T;\varepsilon1,\varepsilon2,\varepsilon3,\varepsilon4,\varepsilon5;7;200) = [E_T^i C_{PM2.5}^i, E_T^i C_{PM10}^i,$$
$$E_T^i C_{CO}^i, E_T^i C_{NO2}^i, E_T^i C_{SO2}^i, E_T^i C_{O3}^i, E_T^i AQI^i]_{200}^{i=\varepsilon1,\varepsilon2,\varepsilon3,\varepsilon4,\varepsilon5}$$

a training output of the model is a 7-dimensional index set R(C; 7; 200) of the outdoor air quality monitoring data of the train in 200 continuous moments in the data set, thereby obtaining a well-trained deep belief network to learn a nonlinear mapping relationship between the outdoor air pollutants of the train and the spatially related monitoring stations. The input-output relationship of the model is recorded as $$R(C;7;200) = f\left[\underset{ER}{\Leftrightarrow}(T;\varepsilon1,\varepsilon2,\varepsilon3,\varepsilon4,\varepsilon5;7;200)\right]$$

S5. perform short-term prediction on air pollutant concentrations of the position where the train is located by using the spatial mixture model for multi-pollutant concentration indexes established in the step S4;

in specific implementations, the trained spatial mixture model for multi-pollutant concentration indexes is used for performing short-term prediction on the outdoor air pollutant concentrations of the train, and a predicted result of air pollutant index of each monitoring station is combined with the degradation degree at the corresponding moment to serve as the input of the spatial mixture model for multi-pollutant concentration indexes:

$$[E_T^i\hat{C}_{PM2.5}^i, E_T^i\hat{C}_{PM10}^i, E_T^i\hat{C}_{CO}^i, E_T^i\hat{C}_{NO2}^i, E_T^i\hat{C}_{SO2}^i,$$
$$E_T^i\hat{C}_{O3}^i, E_T^i\hat{AQI}^i]_{T=12,30,45,60\ min}^{i=\varepsilon1,\varepsilon2,\varepsilon3,\varepsilon4,\varepsilon5}$$

by inputting it into the model, a result of the short-term prediction of the outdoor air pollutant concentrations of the train is obtained:

$$R(C;7;T) = f\{[E_T^i\hat{C}_{PM2.5}^i, E_T^i\hat{C}_{PM10}^i, E_T^i\hat{C}_{CO}^i, E_T^i\hat{C}_{NO2}^i,$$
$$E_T^i\hat{C}_{SO2}^i, E_T^i\hat{C}_{O3}^i, E_T^i$$
$$\hat{AQI}^i]^{i=\varepsilon1,\varepsilon2,\varepsilon3,\varepsilon4,\varepsilon5}\}_{T=12,30,45,60\ min}$$

wherein R(C; 7; T) is the 7-dimensional index set after 15 minutes, 30 minutes, 45 minutes and 60 minutes, including predicted results of outdoor PM2.5, PM10, CO, $NO_2$, $SO_2$ and $O_3$ concentrations and AQI of the train;

S6. perform early warning on an air environment of the train according to a result of the short-term prediction in the step S5; specifically, it is to perform the early warning in the following rules:

If predicted AQI values of an area passed by the train are smaller than or equal to 100 within a plurality of future moments, an air pollution level is predicted to be 0, indicating that the outdoor air quality of the train is still acceptable, no treatment measures will be taken, and air quality monitoring and prediction will be continued; and the early warning will not be performed;

If the predicted AQI values of the area passed by the train are greater than 100 but smaller than or equal to 200 within the plurality of future moments, the air pollution level is predicted to be 1; a level-1 early warning will be performed; susceptible population among the passengers on the train can be alerted to pay attention to the indoor air quality pollution of the train and the time remaining until the next door opening and closing event of the train can be broadcast, so that the susceptible population can wear a mask in advance to avoid irritative symptoms; and if the predicted AQI values of the area passed by the train are greater than 200 within the plurality of future moments, the air pollution level is predicted to be 2; a level-2 early warning will be performed; and all the passengers on the train can be alerted to pay attention to the indoor air quality pollution of the train and the time remaining until the next door opening and closing event of the train can be broadcast, so that the susceptible population can wear a mask in advance to avoid uncomfortable symptoms.

Meanwhile, after an early warning is completed, each monitoring station continuously detects the air quality index and uploads it to a control end; in particular, due to train operation, diffusion effects of air pollutants, and occurrence of extreme weather conditions, the model needs to be regularly re-trained to ensure the accuracy of the early warning. The time interval of re-training is the same as the time interval of air quality data acquisition and update, preferably set as 1 hour.

The present invention has the following advantages:

the present invention crawls real-time updated monitoring data of the China National Environmental Monitoring Center by using an incremental network crawler; and the crawling period is set to be the time difference between two updates of the same url on the China National Urban Air Quality Real-time Publishing Platform, thereby analyzing the national air pollutant indexes published at each hour; by mastering pollutant indexes of the monitoring stations surrounding the forward running area of the train according to spatial distribution of the monitoring stations, and by sufficiently taking advantage of existing urban pollutant monitoring data, the method plays a guiding role in early warning of air pollution conditions of train operation; and longitude and latitude information can be acquired by performing real-time positioning on the current position of the train; a predicted position of the train after a certain period of time is calculated by combining the speed and running route of the train, the train-station distance and historical sequence association are subjected to fusion analysis by using the diffusion factor, and a fusion result is defined as a degradation degree index for screening out the monitoring stations imposing the greatest degradation degree on the outdoor air quality of the train after the certain period of time, thereby providing a spatially related data set for the outdoor air environment analysis of the train.

According to the spatially related data set obtained through screening, the monitoring station air pollutant prediction module is established to predict concentrations of PM2.5, PM10, CO, $NO_2$, $SO_2$ and $O_3$ and AQI in different time steps; a deep neural network is used for establishing a spatial mixture model for the pollutant concentration indexes of a plurality of air quality monitoring stations along the railway, thereby effectively acquiring the outdoor air pollution situation of the position where the train is located after the certain period of time.

By combining a result of short-term prediction of the outdoor air quality index of the train and geographical location information of the train, graded early warning measures are taken for health protection of the passengers on the train, and different early warning information is provided for susceptible population and healthy population on the train.

What is claimed is:

1. A health early warning method for passengers on a train in an outdoor air polluted environment, which is implemented by a health early warning system for the passengers on the train in the outdoor air polluted environment the health early warning system for the passengers on the train in the outdoor air polluted environment comprises an air quality monitoring station data acquisition module, a train data acquisition module, a train air pollution prediction module and a train air environment early warning module, wherein an output end of the air quality monitoring station data acquisition module and an output end of the train data acquisition module are both connected with an input end of the train air pollution prediction module; an output end of the train air pollution prediction module is connected with the train air environment early warning module; the air quality monitoring station data acquisition module is configured to acquire data information of air quality monitoring stations and upload the data information of air quality monitoring stations to the train air pollution prediction module; the train data acquisition module is configured to acquire data information of the train and upload the data information of the train to the train air pollution prediction module; the train air pollution prediction module is configured to perform a short-term prediction on air pollution of the train according to the uploaded data information and upload a predicted result to the train air environment early warning module; and the train air environment early warning module is configured to perform an air environment early warning according to the predicted result, thereby performing an early warning on an air environment of the train and on health of the passengers on the train; and the health early warning method for the passengers on the train in the outdoor air polluted environment comprises the following steps:

S1. acquire the data information of each air quality monitoring station and corresponding air quality monitoring data of the each air quality monitoring station;

S2. acquire pollutant data information of a position where the train is located and position information of the train;

S3. perform a train-air quality monitoring station coupling analysis according to data acquired in the steps S1 and S2, thereby screening out a plurality of associated air quality monitoring stations; wherein the step S3 is, specifically, to perform a coupling analysis and screen out the associated air quality monitoring stations in the following steps:

A. calculate a predicted position of the train after future T minutes by using the following equation, wherein T is a positive integer:

$$LOC_T^C = [LOT^C + T \times v \times \vec{r}_{LOT}, LAT^C + T \times v \times \vec{r}_{LAT}]$$

wherein, $LOC_T^C$ is longitude and latitude information of the predicted position of the train after the future T minutes; $LOT^C$ is current longitude information of the train, $LAT^C$ is current latitude information of the train, v is the information of average speed per minute of the train in past several minutes, $\vec{r}_{LOT}$ is a longitude unit vector of the directed path of the remaining running route of the train, and $\vec{r}_{LAT}$ is a latitude unit vector of the directed path of the remaining running route of the train;

B. calculate a distance between the train and the each air quality monitoring station after the future T minutes;

C. calculate, by using the following equation, mutual information between the pollutant data information on a train side and the air quality monitoring data of the each air quality monitoring station at a plurality of continuous moments, thereby obtaining a deterministic association index set between the train side and the each air quality monitoring station:

$$MI(A_{200}^C; A_{200}^{S,i}) = \sum_{a \in A_{200}^C} \sum_{b \in A_{200}^{S,i}} P(a, b) \log \frac{P(a, b)}{P(a)P(b)} = H(A_{200}^C) - H(A_{200}^C \mid A_{200}^{S,i})$$

wherein, $A_{200}^C$ is an AQI sequence on the train side in 200 continuous moments, $A_{200}^{S,i}$ is an AQI value of the i-th air quality monitoring station; P(a,b) is a joint probability distribution function of random variables $A_{200}^C$ and $A_{200}^{S,i}$, P(a) is a marginal probability distribution function of $A_{200}^C$, P(b) is a marginal probability distribution function of $A_{200}^{S,i}$ $H(A_{200}^C)$ is a marginal entropy, and $H(A_{200}^C \mid A_{200}^{S,i})$ is a conditional entropy; and D. analyze and select the plurality of associated air quality monitoring stations with a greatest environmental impact on the train side after the T minutes according to the distance between the train and the each air quality monitoring station;

S4. establish a spatial mixture model for multi-pollutant concentration indexes according to the plurality of associated air quality monitoring stations screened out in the step S3;

S5. perform the short-term prediction on air pollutant concentrations of the position where the train is located by using the spatial mixture model for multi-pollutant concentration indexes established in the step S4; and S6. perform the early warning on the air environment of the train according to a result of the short-term prediction in the step S5.

2. The method according to claim 1, wherein the step of acquiring the data information of the each air quality monitoring station and the corresponding air quality monitoring data of the each air quality monitoring station in the step S1 is, specifically, to acquire code information, longitude and latitude information, as well as corresponding information of concentrations of PM2.5, PM10, CO, $NO_2$, $SO_2$ and $O_3$ and AQIs of the each air quality monitoring station.

3. The method according to claim 2, wherein the step of acquiring the pollutant data information of the position where the train is located and the position information of the train in the step S2 is, specifically, to acquire longitude and latitude information, information of concentrations of PM2.5, PM10, CO, $NO_2$, $SO_2$ and $O_3$ of the position where the train is located, and information of average speed per minute of the train in past several minutes, and information of a directed path of a remaining running route of the train.

4. The method according to claim 3, wherein the step of analyzing and selecting the plurality of associated air quality monitoring stations with the greatest environmental impact on the train side after the T minutes in the step D is, specifically, to perform analysis and selection in the following steps:

a. calculate a degradation degree $E_T^i$ imposed by the each air quality monitoring station on air quality on the train side after the T minutes by using the following equation:

$$E_T^i = \frac{p}{Nd_T^i} + (1 - p) \times NMI(A_{200}^C; A_{200}^{S,i})$$

wherein, $Nd_T^i$ is a relative distance between a normalized air quality monitoring station i and the train after the T minutes; p is a diffusion factor; and $NMI(A_{200}^C; A_{200}^{S,i})$ is mutual information between the normalized air quality monitoring station i and the train;

b. optimize a value of the diffusion factor by using a multi-objective and multi-verse optimization algorithm; and c. select, according to the degradation degree calculated in the step a, a plurality of air quality monitoring stations imposing a greatest degradation degree as final air quality monitoring stations with the greatest environmental impact on the train side.

5. The method according to claim 4, wherein the step of optimizing the value of the diffusion factor by using the multi-objective and multi-verse optimization algorithm in the step b is, specifically, to perform optimization in the following steps:

(1) establish a single-variable optimization model, wherein an optimization variable is the diffusion factor p;

(2) initialize the multi-objective and multi-verse optimization algorithm, and set an algorithm parameter;

(3) arrange and archive all universe groups by expansion rate;

(4) screen out an optimal universe from a Pareto solution set as a universal leader;

(5) open a black-white hole tunnel and a wormhole tunnel, wherein objects in universe can pass through the black-white hole tunnel and the wormhole tunnel self-adaptively until a lower expansion rate is acquired; and (6) determine a search frequency:

if the search frequency reaches a set threshold, output an optimal solution for determining the value of the diffusion factor;

otherwise, add 1 to the search frequency, and repeat the steps (3) to (6) until the search frequency reaches the set threshold.

6. The method according to claim 5, wherein the step of establishing the spatial mixture model for multi-pollutant concentration indexes in the step S4 is, specifically, to establish the spatial mixture model for multi-pollutant concentration indexes in the following steps:

1) acquire air quality data information of the associated air quality monitoring stations and the pollutant data information on the train side;

2) divide data acquired in the step 1) into a training set and a verification set;

3) train a predictor model by taking the air quality data information of the associated air quality monitoring stations as an input of the predictor model, and by taking the pollutant data information on the train side after a Δt moment as an output of the predictor model, thereby obtaining a pollutant concentration prediction model for the associated air quality monitoring stations in a step of Δt;

4) perform, according to the pollutant concentration prediction model for the associated air quality monitoring stations obtained in the step 3), a plurality of steps of prediction on air quality of positions where the associated air quality monitoring stations are located, thereby obtaining an air quality prediction set of the associated air quality monitoring stations; and 5) train and establish a deep belief network model by taking a multiplication combination term of the air quality data information of the associated air quality monitoring stations and a degradation degree imposed by the associated air quality monitoring stations on the air quality on the train side after the T minutes as an input of the deep belief network model and by taking the pollutant data information on the train side as an output of the deep belief network model, thereby obtaining the spatial mixture model for multi-pollutant concentration indexes.

7. The method according to claim 6, wherein the step of obtaining the pollutant concentration prediction model for the associated air quality monitoring stations in the step of Δt in the step 3) is, specifically, to use a GMDH predictor as the predictor model, which uses a Kolmogorov-Gabor polynomial as a support function; a topological structure of the GMDH predictor comprises 3 layers, and the predictor model selects a plurality of neurons as an input of the next layer after a first layer is formed; a number of neurons in each layer is limited to 100; and the following equation is used as an evaluation function:

$$evaluation = \sum_{i=1}^{3} n_i + MSE$$

wherein, $n_i$ is the number of neurons in the i-th layer in the GMDH predictor, and MSE is a mean square error predicted by the prediction model on the verification set.

8. The method according to claim 7, wherein the step of performing the early warning on the air environment of the train in the step S6 is, specifically, to perform the early warning in the following rules:

if predicted AQI values of an area passed by the train are smaller than or equal to 100 within a plurality of future moments, an air pollution level is predicted to be 0, and the early warning will not be performed;

if the predicted AQI values of the area passed by the train are greater than 100 but smaller than or equal to 200 within the plurality of future moments, the air pollution level is predicted to be 1, and a level-1 early warning will be performed; and if the predicted AQI values of the area passed by the train are greater than 200 within the plurality of future moments, the air pollution level is predicted to be 2, and a level-2 early warning will be performed.

* * * * *